(12) United States Patent
Spruit et al.

(10) Patent No.: US 10,379,028 B2
(45) Date of Patent: Aug. 13, 2019

(54) LASER SENSOR FOR MULTI PARAMETER DETECTION

(71) Applicant: PHILIPS PHOTONICS GMBH, Ulm (DE)

(72) Inventors: Johannes Hendrikus Maria Spruit, Eindhoven (NL); Alexander Marc Van Der Lee, Eindhoven (NL); Gerben Kooijman, Eindhoven (NL); Okke Ouweltjes, Eindhoven (NL); Joachim Wilhelm Hellmig, Eindhoven (NL); Arnoldus Johannes Martinus Jozeph Ras, Eindhoven (NL); Petrus Theodorus Jutte, Eindhoven (NL)

(73) Assignee: PHILIPS PHOTONICS GMBH, Ulm (DE)

( * ) Notice: Subject to any disclaimer, the term of this patent is extended or adjusted under 35 U.S.C. 154(b) by 0 days.

(21) Appl. No.: 15/748,207

(22) PCT Filed: Jul. 15, 2016

(86) PCT No.: PCT/EP2016/066873
§ 371 (c)(1),
(2) Date: Jan. 29, 2018

(87) PCT Pub. No.: WO2017/016901
PCT Pub. Date: Feb. 2, 2017

(65) Prior Publication Data
US 2018/0224368 A1 Aug. 9, 2018

(30) Foreign Application Priority Data
Jul. 30, 2015 (EP) .................................. 15179027

(51) Int. Cl.
*G01N 15/14* (2006.01)
*G01S 17/58* (2006.01)
*G01S 17/95* (2006.01)
(Continued)

(52) U.S. Cl.
CPC ..... *G01N 15/1434* (2013.01); *G01B 9/02092* (2013.01); *G01N 15/0205* (2013.01);
(Continued)

(58) Field of Classification Search
CPC ........... G01N 15/1434; G01N 15/0205; G01N 15/06; G01N 2015/03; G01B 9/02092; G01S 7/4802; G01S 7/4916; G01S 17/08
USPC ..... 356/601–623, 5.15, 5.01, 5.1, 4.05, 28.5
See application file for complete search history.

(56) References Cited

U.S. PATENT DOCUMENTS 5,587,785 A 12/1996 Kato et al.
6,233,045 B1 * 5/2001 Suni ........................ G01C 3/08
356/28.5
(Continued)

FOREIGN PATENT DOCUMENTS

| CN | 103868835 A | 6/2014 |
| WO | 0237411 A1 | 5/2002 |
| WO | 2014167175 A1 | 10/2014 |

OTHER PUBLICATIONS

Giuliani et al "Laser Diode Self-Mixing Technique for Sensing Applications" Journal of Optics, 2002 p. 283-294.
(Continued)

*Primary Examiner* — Hoa Q Pham
(74) *Attorney, Agent, or Firm* — Leydig, Voit & Mayer, Ltd.

(57) ABSTRACT

The invention describes a laser sensor module (100) which is adapted to detect or determine at least two different physical parameters by means of self-mixing interference by focusing a laser beam to different positions. Such a laser sensor module (100) may be used as an integrated sensor module, for example, in mobile devices (250). The laser sensor module (100) may be used as an input device and in addition as a sensor for detecting physical parameters in an environment of the mobile communication device (250). One physical parameter in the environment of the mobile communication device (250) may, for example, be the concentration of particles in the air (air pollution, smog . . . ). The invention further describes a related method and computer program product.

20 Claims, 6 Drawing Sheets

(51) Int. Cl.
    G01B 9/02      (2006.01)
    G01N 15/02     (2006.01)
    G01N 15/06     (2006.01)
    G01S 7/48      (2006.01)
    G01S 7/491     (2006.01)
    G01S 17/87     (2006.01)
    G01S 7/481     (2006.01)
    G01N 15/10     (2006.01)

(52) U.S. Cl.
    CPC ............ *G01N 15/06* (2013.01); *G01S 7/4802* (2013.01); *G01S 7/4812* (2013.01); *G01S 7/4817* (2013.01); *G01S 7/4916* (2013.01); *G01S 17/58* (2013.01); *G01S 17/87* (2013.01); *G01S 17/95* (2013.01); *G01N 2015/0693* (2013.01); *G01N 2015/1075* (2013.01); *G01N 2015/1438* (2013.01); *G01N 2015/1452* (2013.01); *G01N 2015/1454* (2013.01); *G01N 2015/1493* (2013.01); *Y02A 90/19* (2018.01)

(56) References Cited

U.S. PATENT DOCUMENTS

| | | | |
|---|---|---|---|
| 7,317,513 B2* | 1/2008 | Sesko | G01S 17/32 356/4.01 |
| 7,889,353 B2* | 2/2011 | Schemmann | G06F 3/0421 356/498 |
| 7,994,468 B2* | 8/2011 | Duijve | G06F 3/0346 250/221 |
| 8,107,056 B1* | 1/2012 | Riza | G01C 3/32 356/4.05 |
| 2009/0303458 A1 | 12/2009 | Heinks et al. | |
| 2011/0007299 A1 | 1/2011 | Moench et al. | |
| 2012/0002189 A1 | 1/2012 | Bengoechea et al. | |
| 2013/0063718 A1 | 3/2013 | Bernal et al. | |
| 2013/0120759 A1 | 5/2013 | Van Der Lee | |
| 2013/0215411 A1 | 8/2013 | Christian et al. | |
| 2014/0085635 A1 | 3/2014 | Van Der Lee | |
| 2014/0132943 A1 | 5/2014 | Chou | |
| 2015/0077735 A1 | 3/2015 | Zamama et al. | |
| 2018/0209779 A1* | 7/2018 | Van Der Lee | G01S 17/32 |
| 2018/0209892 A1* | 7/2018 | Van Der Lee | G01S 17/58 |

OTHER PUBLICATIONS

Sudo et al "Detection of Small Particles in Fluid Flow Using a Self-Mixing Laser" Optical Express, vol. 15, No. 13, June 25, 2007, p. 8135-8145.

* cited by examiner

LASER SENSOR FOR MULTI PARAMETER DETECTION

CROSS-REFERENCE TO PRIOR APPLICATIONS

This application is the U.S. National Phase application under 35 U.S.C. § 371 of International Application No. PCT/EP2016/066873, filed on Jul. 15, 2016, which claims the benefit of EP Patent Application No. EP 15179027.6, filed on Jul. 30, 2015. These applications are hereby incorporated by reference herein.

FIELD OF THE INVENTION

The invention relates to a laser sensor or laser sensor module using self-mixing interference for detection of different physical parameters, a user interface comprising such a laser sensor or laser sensor module, a mobile communication device comprising such a user interface, a related method of detection of different physical parameters and a corresponding computer program product.

BACKGROUND OF THE INVENTION

CN103868835 (A) discloses a system for monitoring PM2.5 by a smart phone. The system is provided with a small and intelligent air sampling head. The intelligent air sampling head can perform inhaling sampling through a human mouth and also can perform sampling by a sampling air pump. The intelligent air sampling head and the smart phone can communicate with each other. The intelligent air sampling head measures the number and particle size of dust in air by a laser scattering method under the guide of the smart phone. The system is complicated and expensive.

US 2013/0120759 A1 discloses an apparatus for measuring a distance. A self-mixing interference (SMI) unit generates an SMI signal, wherein the SMI unit comprises a laser emitting a first laser beam for being directed to an object and wherein the SMI signal depends on an interference of the first laser beam and a second laser beam reflected by the object. A peak width determination unit determines a peak width of the SMI signal, and a distance determination unit determines a distance between the object and the SMI unit depending on the determined peak width of the SMI signal.

US 2015/0077735 A1 discloses a device for determining wind speed comprises at least two laser sources emitting beams in different directions that are coplanar and such that each emission direction corresponds to a perpendicular emission direction. Each laser source is associated with focusing optics for focusing the emitted beam, a laser diode for receiving a reflected beam obtained after reflection by a particle present in the air of the corresponding emitted beam, a photodiode for transmitting an interference signal occurring between the emitted beam and the reflected beam, a processor for processing the obtained interference signals, and an optical cavity into which the reflected beam is reinjected in order to obtain an interference with the emitted beam.

US 2013/0215411 A1 discloses a laser Doppler velocimeter using self-mixing amplification from backreflections from scatterers below a surface of a flow.

WO 2014/167175 A1 discloses a velocimeter which comprises a laser source comprising a laser cavity for producing a continuous-wave laser beam, a light detector, and means for directing a first portion of the laser beam to a moving target outside the velocimeter for producing scattered light from the target, the scattered light exhibiting a Doppler shift corresponding to the speed of the moving target. Further, the velocimeter comprises means for guiding scattered light back to the laser cavity for providing frequency-modulation of the laser beam through perturbance in the laser source, and means for guiding a second portion of the laser beam to the light detector. There is further provided an optical edge filter adapted to demodulate said frequency-modulated laser beam before guiding to the light detector and wherein said laser source is adapted to produce laser light at a wavelength corresponding to the wavelength of the edge of the optical edge filter.

SUMMARY OF THE INVENTION

It is an object of the present invention to provide an improved laser sensor module.

According to a first aspect a laser sensor module is provided. The laser sensor module comprises at least one first laser, at least one first detector, at least one electrical driver and at least one first optical device. The first laser is adapted to emit first laser light in reaction to signals provided by the at least one electrical driver. The first optical device is adapted to focus the first laser light to a focus region. The laser sensor module is adapted to control a distance between the laser sensor module and the focus region such that there are at least a first mode and a second mode of the laser sensor module. The laser sensor module is therefore arranged such that there are at least two different focus regions. The focus region is in the first mode at a first distance and in the second mode is the focus region at a second distance different than the first distance. The at least one first detector is adapted to detect a first self-mixing interference signal of an optical wave within a first laser cavity of the first laser. The first self-mixing interference signal is caused by first reflected laser light reentering the first laser cavity. The first reflected laser light is received in the first mode. The first self-mixing interference signal is used to determine a first physical parameter. The laser sensor module especially the at least one first sensor is adapted to detect a second self-mixing interference signal, wherein the second self-mixing interference signal is caused by second reflected laser light. The second self-mixing interference signal is determined in the second mode. The second self-mixing interference signal is used to determine a second physical parameter different than the first physical parameter.

The first laser may preferably be adapted to emit laser light with wavelength above 750 nm in the infrared range of the spectrum, most preferably between 780 nm and 1300 nm of the wavelength spectrum.

The first laser may be a semiconductor laser as side emitter or a Vertical Cavity Surface Emitting laser (VCSEL).

The second self-mixing interference signal may be determined or detected within the first laser cavity of the first laser. Alternatively, there may be at least a second laser with the second laser cavity in which the second self-mixing interference signal may be determined. The first detector may be integrated in the first laser. The first detector may, for example, be a photodiode which is comprised by a layer structure of the first laser. The first detector may alternatively be an external detector which may be adapted to determine, for example, the impedance of the at least first laser cavity for determining at least the first self-mixing interference signal. The first detector may be external photodiode receiving laser light from the first laser, wherein the laser light comprises information about the first self-mixing interference signal. The laser light may, for example, be modulated due to the interference in the first laser cavity.

The first physical parameter is related to the movement of an object for gesture control. The second physical parameter is related to a detection of a particle. The first physical parameter may, for example, comprise distance and/or velocity of the object relative to the laser sensor module. The detection of the particle or particles comprises particle density in a fluid as, for example, air, particle size and optionally speed of the particle. The speed of the particle may for example be used to determine wind speed. Detection of the particle size and/or particle density may be used for event recognition (being behind a truck with dirty fumes, or cooking, or vacuum cleaning, . . . ). For a particle counter the first laser light may be focused to a point to increase the self-mixing signal for small particles, the measurement volume is small and a movable mirror (e.g. MEMs mirror) may be used to scan the spot and to obtain an increased measurement volume. A quasi-collimated beam of first laser light may be used for gesture control. One of the focus regions may be approximately in infinity (essentially parallel beams).

The laser sensor module may comprise a manipulation unit. The manipulation unit may be adapted to change a characteristic of the first laser light such that the first and the second mode are enabled.

The laser sensor module may comprise a controller. The controller may be adapted to provide control signals for controlling the manipulation unit such that the first laser light is focused in a first focus region in the first mode and such that the first laser light is focused in a second focus region in the second mode. The controller may be an integrated part of the manipulation unit or a separate entity.

The laser sensor module may further comprise at least a second laser, wherein the second laser may be adapted to emit second laser light in reaction to signals provided by the at least one electrical driver. A first optical distance between the first laser and the first optical device may be different than a second optical distance between the second laser and the first optical device. The manipulation unit may be adapted to image the first laser light by means of the first optical device to a first focus region in the first mode. The manipulation unit may be adapted to focus the second laser light by means of the first optical device to a second focus region different than the first focus region in the second mode.

The manipulation unit may be an active or passive device. The manipulation unit may, for example, comprise one or more mirrors which are adapted to redirect first laser light and second laser light to the first optical device. The manipulation unit may alternatively comprise a semitransparent mirror such that first laser light and second laser light may reach the first optical device at the same time. The manipulation unit may in an alternative approach comprise a polarizing beam splitter. The first and the second laser light may be polarized laser light. The laser sensor module may comprise control circuitry which may be adapted to switch the first and the second laser in and out in an alternating order to provide the first and the second mode at different moments in time.

The first optical device may comprise the manipulation unit. The manipulation unit may be adapted to provide at least a first focal length of the first optical device and a second focal length of the first optical device different than the first focal length. The controller may be adapted to provide control signals for controlling the manipulation unit such that the first optical device provides the first focal length in the first mode and the second focal length in the second mode. The manipulation unit in combination with the first optical device may comprise a lens with adaptable focus which is controlled by means of the controller. The lens with adaptable focus may, for example, be based on electrowetting or liquid-crystals. The manipulation unit in combination with the first optical device may alternatively comprise a lens arrangement. The distance between different lances of the lens arrangement may be controlled by means of the controller in order to focus the first laser light to different focus regions. Functionalities of the manipulation unit, controller or electrical driver may be provided by separate units or by integrated units.

The manipulation unit may be adapted to change an optical distance between the first laser and the first optical device. The manipulation unit may especially be adapted to change a distance between the first laser and the first optical device. The manipulation unit may, for example, comprise a device to shift the first laser and/or the first optical device relative to each other.

The manipulation unit may alternatively or in addition comprise a second optical device. The second optical device may be adapted to change the optical distance between the first laser and the first optical device. The second optical device may comprise, for example, one or more mirrors, wherein at least one of the mirrors is adapted to change the path of the first laser light between the first laser and the first optical element.

The first optical device may alternatively or in addition comprise at least one birefringent element for enabling the first mode and the second mode. The first optical device may be one optical unit or comprise two or more optical units. The birefringent element may comprise LiNbO3 (Lithium Niobate). The birefringent element may comprise a non-periodic phase structure or a periodic diffractive structure.

A non-periodic phase structure may, for example, be provided in a birefringent material such that for 1 polarization direction the effect is negligible as only 2 pi phase steps are made and for the other polarization direction an additional lens power is added such that laser light with this polarization is focused differently. The laser sensor module may be adapted to emit laser light with the first and a second polarization. The second polarization is different than the first polarization. The second polarization is preferably orthogonal to the first polarization.

The laser sensor module may further comprise a controller. The first laser may be adapted to emit the first laser light with a first polarization and the first laser light with a second polarization different than the first polarization. The controller may be adapted to provide control signals for controlling the first laser such that the first laser emits the first laser light with the first polarization in the first mode and the first laser light with the second polarization in the second mode. The birefringent element may be adapted to focus the first laser light with the first polarization to a first focus region. The birefringent element may be further adapted to focus the first laser light with the second polarization to a second focus region different than the first focus region.

The controller may, for example, periodically switch between the first and the second polarization in alternating order. The controller may in an alternative approach switch between the first and second polarization upon receiving respective additional control signals. The first laser may comprise a switchable polarization device in order to provide the first and second polarization. The first laser may, for example, be a VCSEL wherein transversal voltage may be applied to a mesa of the VCSEL. The first laser may alternatively comprise a switchable polarization rotator which may be controlled by means of the control signals provided by the controller. The switchable polarization rotator may, for example, be an electro-optical element as a liquid-crystal cell.

The laser sensor module may further comprise at least a second laser. The second laser may be adapted to emit second laser light in reaction to signals provided by the at least one electrical driver via the first optical device. The first laser light may comprise a first polarization and the second laser light may comprise a second polarization different than the first polarization. The birefringent element is adapted to focus the first laser light to a first focus region in the first mode. The birefringent element is adapted to focus the second laser light to a second focus region different than the first focus region in the second mode.

The first self-mixing interference signal is in this case independent from the second self-mixing interference signal which is present in the second laser cavity of the second laser. The first self-mixing interference signal and the second self-mixing interference signal may thus be determined at the same time or in alternating order or depending on a corresponding trigger signal.

The first optical device may alternatively or in addition be adapted to focus a first part of the first laser light to a first focus region and a second part of the first laser light to a second focus region. The first optical device may, for example, comprise a segmented lens. A first segment of the segmented lens may focus the first laser light to the first distance. A second segment of the segmented lens may focus the first laser light to the second distance.

The first laser may be adapted to emit the first laser light with a first emission pattern in the first mode. The first laser may be further adapted to emit the first laser light with a second emission pattern in the second mode. The first laser may therefore be adapted to illuminate different parts of the first optical device by means of the first and second emission pattern. Furthermore, there may be additional optical devices such as an adaptable mirror or mirrors which may be used in order to illuminate different parts of the first optical device.

The first laser may, for example, be a VCSEL which can preferably emit a centered mode (like Gaussian) or a donut mode. It is known that the preferred modes within a laser cavity of the VCSEL changes with current. At lower current the centered mode may be more prominent and at higher current the donut. This means that two different operating points can be used for the VCSEL for the first and the second mode. The VCSEL may, for example, comprise multiple oxide apertures or a surface relief to separate the two operation modes and to stabilize a well-defined mode of operation. Alternatively or in addition the fact can be used that the emission pattern of the VCSEL gets broader at higher currents (because of the stronger thermal lens). Therefore at an operating point with higher current more of the outer region of the segmented lens may be used. The electrical driver may be adapted to supply the different currents.

The laser sensor module may further comprise at least a second laser. The second laser may be adapted to emit second laser light in reaction to signals provided by the at least one electrical driver via the first optical device, wherein the first laser light comprises a first wavelength and the second laser light comprises a second wavelength different than the first wavelength. The first optical device maybe adapted to focus the first laser light to a first focus region in the first mode. The first optical device may be further adapted to focus the second laser light to a second focus region different than the first focus region in the second mode.

The first optical device may, for example, comprise a wavelength selective non-periodic structure or diffractive structure.

The first laser may in an alternative approach be adapted to emit light of different wavelengths. The first laser may be adapted to switch between the first and the second wavelength by means of corresponding control signals in order to enable the first and the second mode.

A human interface device may comprise at least one laser sensor module in accordance with any embodiment described above. The first mode of the laser sensor module may be adapted to enable at least a part of input features provided by the human interface device.

The laser sensor module may, for example, be integrated in a touch screen or other input device. The first mode may be used to support detection of, for example, a finger moving across at least a part of the touch screen. The first mode may alternatively or in addition be used for gesture control within a defined distance between the laser sensor module and, for example, a hand of the user. The second mode of the laser sensor module may, for example, be used to detect air pollution or more general particles in the air.

A mobile communication device may comprise at least one laser sensor module or at least one human interface device comprising at least one laser sensor module.

According to a further aspect a method of detecting at least two physical parameters is presented. The method comprises the steps of:

emitting first laser light by means of a first laser,
focusing the first laser light to a focus region,
controlling a distance between the laser sensor module and the focus region such that there are at least a first mode and a second mode, wherein in the first mode the focus region is at a first distance and in the second mode the focus region is at a second distance different than the first distance,
receiving first reflected laser light in a first laser cavity of the first laser,
determining a first self-mixing interference signal of an optical wave within the first laser cavity of the first laser, wherein the first self-mixing interference signal is caused by the first reflected first laser light reentering the first laser cavity, the first reflected laser light being received in the first laser cavity in the first mode,
using the first self-mixing interference signal to determine the first physical parameter,
determining a second self-mixing interference signal in the second mode, wherein the second self-mixing interference signal is caused by second reflected laser light,
using the second self-mixing interference signal to determine a second physical parameter different than the first physical parameter.

The steps of the method are not necessarily performed in the order as presented above.

According to a further aspect a computer program product is presented. The computer program product comprises code means which can be saved on at least one memory device of the laser sensor module according to any one of claims 1 to 11 or on at least one memory device of a device comprising the laser sensor module. The code means being arranged such that the method according to claim 14 can be executed by means of at least one processing device of the laser sensor module according to any one of claims 1 to 11 or by means of at least one processing device of the device comprising the laser sensor module. The memory device or the processing device may be comprised by the laser sensor module (electrical driver, controller etc.) and/or the device comprising the laser sensor module. A first memory device and/or first processing device of the device comprising the laser sensor module may interact with a second memory device and/or second processing device comprised by the laser sensor module. The device comprising the laser sensor module may be a human interface device or a mobile communication device.

It shall be understood that the laser sensor module according to any one of claims 1 to 11 and the method of claim 14 have similar and/or identical embodiments, in particular, as defined in the dependent claims.

It shall be understood that a preferred embodiment of the invention can also be any combination of the dependent claims with the respective independent claim.

Further advantageous embodiments are defined below.

BRIEF DESCRIPTION OF THE DRAWINGS

These and other aspects of the invention will be apparent from and elucidated with reference to the embodiments described hereinafter.

The invention will now be described, by way of example, based on embodiments with reference to the accompanying drawings.

In the drawings.

DETAILED DESCRIPTION OF EMBODIMENTS

Various embodiments of the invention will now be described by means of the Figures.

Self-mixing interference is used for detecting movement of and distance to an object. Background information about self-mixing interference is described in "Laser diode self-mixing technique for sensing applications", Giuliani, G.; Norgia, M.; Donati, S. & Bosch, T., Laser diode self-mixing technique for sensing applications, Journal of Optics A: Pure and Applied Optics, 2002, 4, S. 283-S. 294 which is incorporated by reference. Detection of movement of a fingertip relative to a sensor in an optical input device is described in detail in International Patent Application No. WO 02/37410. The disclosure regarding the detection of distance and movement in International Patent Application No. WO 02/37410 is incorporated by reference.

The principle of self-mixing interference is discussed based on the examples presented in International Patent Application No. WO 02/37410. A diode laser having a laser cavity is provided for emitting a laser, or measuring, beam. At its upper side, the device is provided with a transparent window across which an object, for example a human finger, is moved. A lens, for example, a plano-convex lens is arranged between the diode laser and the window. This lens focuses the laser beam at or near the upper side of the transparent window. If an object is present at this position, it scatters the measuring beam. A part of the radiation of the measuring beam is scattered in the direction of the illumination beam and this part is converged by the lens on the emitting surface of the laser diode and re-enters the cavity of this laser. The radiation re-entering the cavity of the diode laser induces a variation in the gain of the laser and thus in the intensity of radiation emitted by the laser, and it is this phenomenon which is termed the self-mixing effect in a diode laser.

The change in intensity of the radiation emitted by the laser can be detected by a photo diode, provided for this purpose, which diode converts the radiation variation into an electric signal, and electronic circuitry is provided for processing this electric signal.

Movement of the object relative to the measuring beam causes the radiation reflected thereby to undergo a Doppler shift. This means that the frequency of this radiation changes or that a frequency shift occurs. This frequency shift is dependent on the velocity with which the object moves and is of the order of a few kHz to MHz. The frequency-shifted radiation re-entering the laser cavity interferes with the optical wave, or radiation generated in this cavity, i.e. a self-mixing effect occurs in this cavity. Dependent on the amount of phase shift between the optical wave and the radiation re-entering the cavity, the interference will be constructive or negative, i.e. the intensity of the laser radiation is increased or decreased periodically. The frequency of the laser radiation modulation generated in this way is exactly equal to the difference between the frequency of the optical wave in the cavity and that of the Doppler-shifted radiation re-entering the cavity. The frequency difference is of the order of a few kHz to MHz and thus easy to detect. The combination of the self-mixing effect and the Doppler shift causes a variation in behavior of the laser cavity; especially its gain or light amplification varies. The impedance of the laser cavity or the intensity of the radiation emitted by the laser may, for example, be measured, and not only can the amount of movement of the object relative to the sensor (i.e. distance traveled) be evaluated, but the direction of movement can also be determined, as described in detail in International Patent Application No. WO 02/37410.

Figure 1:
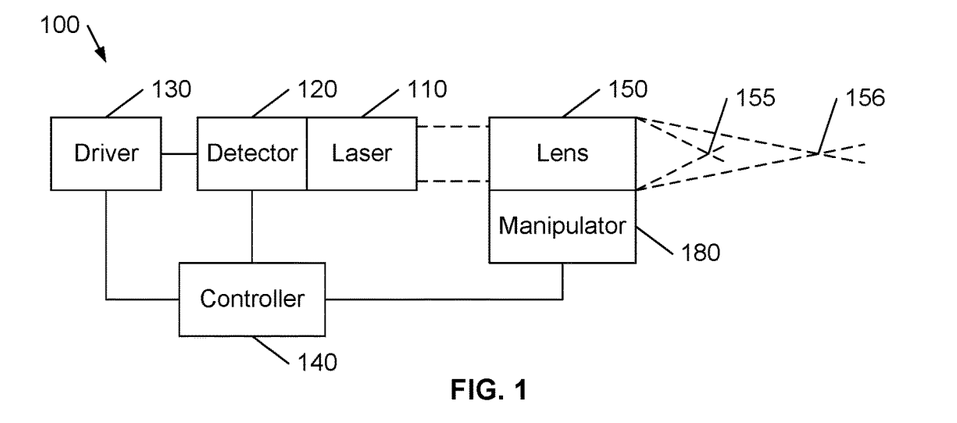
FIG. 1 shows a principal sketch of a first laser sensor module

FIG. 1 shows a principal sketch of a first laser sensor module 100. The first laser sensor module 100 comprises a first laser 110 with an integrated first detector 120. The integrated first detector 120 is an integrated photodiode which is part of the layer structure of the first laser 110. The first laser sensor module 100 further comprises an electrical driver 130, a controller 140 and a manipulation unit 180 comprising a first optical device 150. The controller 140 is connected to the first laser 110 or more precisely the first detector 120 and the electrical driver 130. The electrical driver 130 supplies electrical power to the first laser 110 in order to emit first laser light. The first laser 110 is in this case a Vertical Cavity Surface Emitting Laser (VCSEL) with integrated photodiode. The laser sensor module 100 is connected to a power supply (not shown) which provides the power which is modulated and supplied by means of the electrical driver 130. The electrical driver 130 is adapted to provide a constant driving current or a triangular driving current. The controller 140 is further connected to the manipulation unit 180 in order to provide control signals to change a focal lengths of the first optical device 150. The first optical device 150 is in this case electro wetting lens. The controller 140 is further adapted to receive electrical signals provided by the first detector 120 which are caused by the first self-mixing interference signal or the second self-mixing interference signal. The controller 140 further receives information from the electrical driver 130 and from manipulation unit 180. The first laser light emitted by the first laser 110 is focused by means of the first optical device 150 to a first focus region 155 or second focus region 156 being different from the first focus region. A particle can be detected within a range around the first focus region 155. Gesture control may be enabled if the first laser light is focused to the second focus region 156. The controller 140 may automatically switch between the first and the second mode. Alternatively, the controller 140 may be adapted to switch between the first and the second most of the reception of the respective control signal. The laser sensor module 100 may comprise a switch to provide such control signal to switch between the two modes. Alternatively, the controller 140 may comprise an interface to an external device in order to receive a control signal for switching between the two modes. The electro wetting lens may be placed at a distance such that the 1/e^2 diameter of the Gaussian beam's intensity of the first laser light is between 0.8 and 1.2 mm (wavelength 850 nm). This arrangement may achieve a good self-mixing signal over a long range (0-50 cm) in the second mode. The first mode can be made by adjusting the focal length of the electro wetting lens such that a spot is formed with numerical aperture (NA)~e.g. 0.1. The first laser sensor module 100 may be combined with a movable mirror as discussed below.

Figure 2:
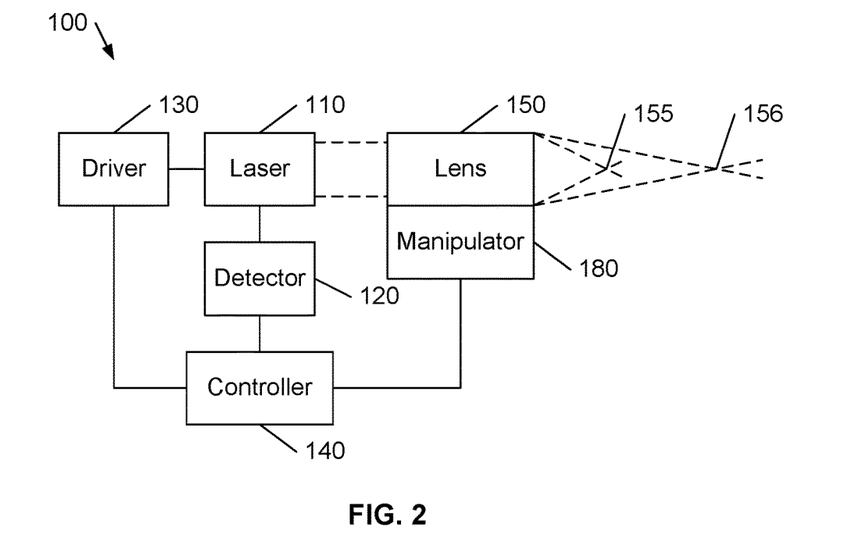
FIG. 2 shows a principal sketch of a second laser sensor module

FIG. 2 shows a principal sketch of a second laser sensor module 100. The second laser sensor module comprises a first laser 110. A first detector 120 is arranged as an external measurement circuit which determines the voltage across the first laser cavity or more generally the impedance of the first laser cavity which is influenced by the first self-mixing interference signal. The second laser sensor module 100 further comprises an electrical driver 130. The electrical driver 130 supplies electrical power to the first laser 110 in order to emit first laser light. The first laser 110 is in this case a side emitting semiconductor laser. The laser sensor module 100 is connected to a power supply (not shown) which provides the power which is modulated and supplied by means of electrical driver 130. The electrical driver 130 is adapted to provide a constant driving current. The controller 140 is further connected to the manipulation unit 180 in order to provide control signals to change a focal lengths of the first optical device 150. The first optical device 150 is in this case an arrangement of lenses which can be shifted with respect to each other. The controller 140 is further adapted to receive electrical signals provided by the first detector 120 which are caused by the first self-mixing interference signal or the second self-mixing interference signal. The controller 140 further receives information from the electrical driver 130. The information with respect to the status of the manipulation unit 180 is taken from the control signals provided to the manipulation unit 180. The first laser light emitted by the first laser 110 is focused by means of the first optical device 150 to a first focus region 155 or second focus region 156 being different from the first focus region. The second laser sensor module 100 can be combined with a movable mirror as discussed below.

Figure 3:
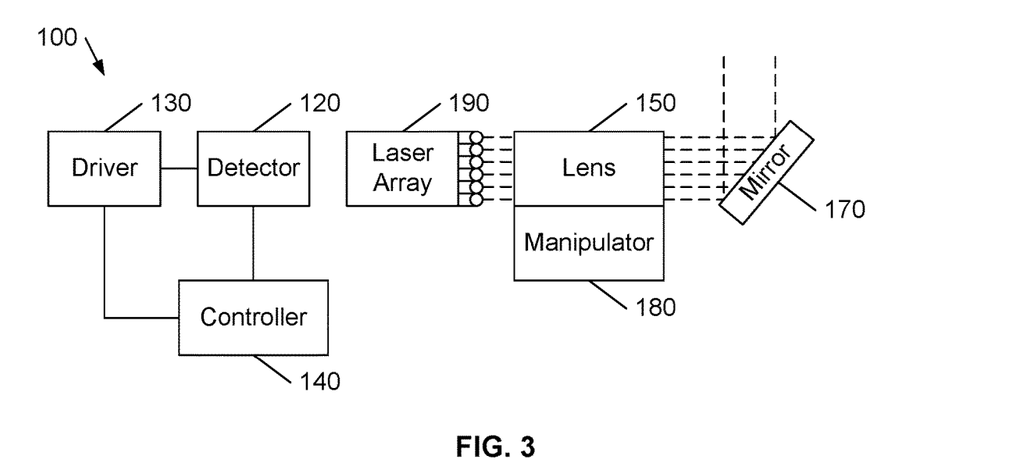
FIG. 3 shows a principal sketch of a third laser sensor module

FIG. 3 shows a principal sketch of a third laser sensor module 100. The third laser sensor module 100 comprises a laser array 190 comprising the first laser 110 and a multitude of other lasers emitting laser light. The third laser sensor module 100 further comprises one common first detector 120, an electrical driver 130, a controller 140, and a manipulation unit 180 comprising a first optical device 150 and a movable mirror 170. The controller 140 is connected to the first detector 120, the electrical driver 130, the manipulation unit 180 and the movable mirror 170. The electrical driver 130 supplies electrical power to the lasers of the laser array in order to emit laser light. Electrical driver 130 may provide a modulated driving current (e.g. rectangular drive current). The controller 140 receives electrical signals provided by the first detector 120 which are caused by the self-mixing interference signals generated within the laser cavities of the lasers of laser array 190. The detector 120 is adapted to identify which laser of laser array 190 generated the self-mixing interference signal. The detector 120 comprises circuitry to determine individually the impedance across the different laser cavities of the lasers of laser array 190. The controller 140 further receives information from the electrical driver 130 and the movable mirror 170 in order to interpret the self-mixing interference signals measured by the first detector 120. The information provided by the electrical driver 130 may comprise the current provided at a predefined moment in time. The controller 140 is further adapted to control movement of the movable mirror 170 by means of corresponding control signals. The control signals provided by controller 140 may determine angular velocity, amplitude of mirror movement and the like. The first optical device 150 is adapted to focus the laser light emitted by the different lasers of the laser array to a first focus region in the first mode and a second focus region in the second mode upon reception of corresponding control signals from controller 140. The first optical device 150 may, for example, comprise an array of micro-lenses. The first optical device 150 may preferably be adapted to focus the laser light to the first or second focus region after being reflected by means of movable mirror 170. The movable mirror increases a detection volume in the first and the second mode.

Figure 4:
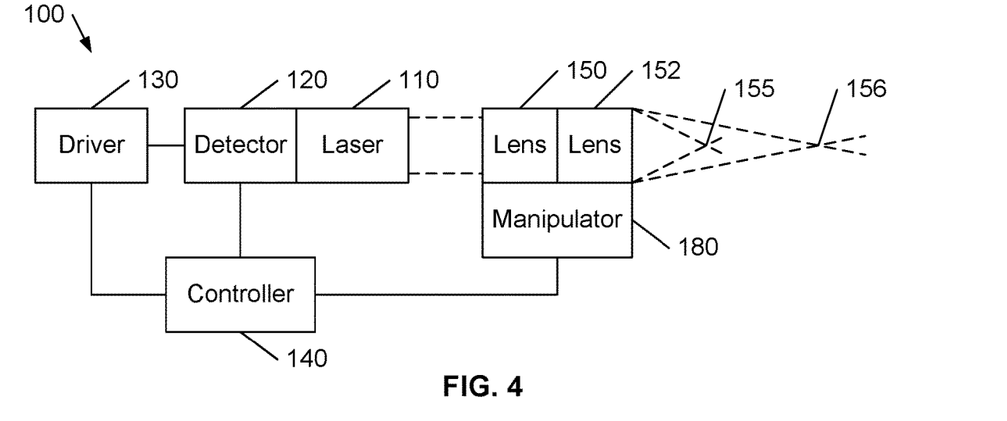
FIG. 4 shows a principal sketch of a fourth laser sensor module

FIG. 4 shows a principal sketch of a fourth laser sensor module 100. The fourth laser sensor module 100 comprises a first laser 110 with an integrated first detector 120. The integrated first detector 120 is an integrated photodiode which is part of the layer structure of the first laser 110. The first laser sensor module 100 further comprises an electrical driver 130, a controller 140, a manipulation unit 180, a first optical device 150 and a birefringent element 152. The controller 140 is connected to the first laser 110 and the electrical driver 130. The electrical driver 130 supplies electrical power to the first laser 110 in order to emit first laser light. The first laser 110 is in this case a Vertical Cavity Surface Emitting Laser (VCSEL) with integrated photodiode. The laser sensor module 100 is connected to a power supply (not shown) which provides the power which is modulated and supplied by means of the electrical driver 130. The electrical driver 130 is adapted to provide a constant driving current or a triangular driving current. The controller 140 is further connected to the manipulation unit 180 in order to provide control signals to change a polarization of the first laser light emitted by the first laser 110.

The manipulation unit 180 is adapted to provide a transversal voltage across the first laser cavity of the first laser 110 in order to switch the polarization. The birefringent element 152 comprises a birefringent material with a non-periodic phase structure. The first laser light is focused to the first focus region 155 if the transversal voltage is applied such that the first laser light is characterized by a first transversal polarization. The first laser light is focused to the second focus region 156 if no transversal voltage is applied by means of manipulation unit 180. The first laser light is in this case characterized by a second transversal polarization being orthogonal to the first transversal polarization. The fourth laser sensor module 100 can be combined with a movable mirror as discussed above.

Figure 5:
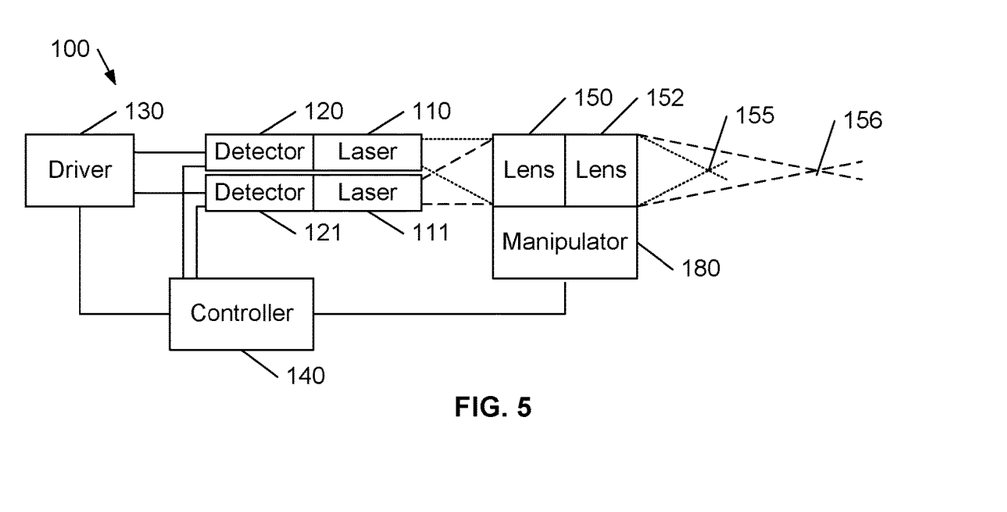
FIG. 5 shows a principal sketch of a fifth laser sensor module

FIG. 5 shows a principal sketch of a fifth laser sensor module 100. The fifth laser sensor module 100 comprises a first laser 110 with an integrated first detector 120 and a second laser 111 with an integrated second detector 121. The first laser 110 emits first laser light with a wavelength of 850 nm being characterized by a first transversal polarization. The second laser 111 emits second laser light with a wavelength of 850 nm being characterized by a second transversal polarization orthogonal to the first transversal polarization. The fifth laser sensor module 100 comprises an electrical driver 130 which is adapted to provide a drive current to the first laser 110 and to the second laser 111. The fifth laser sensor module 100 further comprises a controller 140 which is connected to the first laser 110 and the second laser 111. The fifth laser sensor module 100 further comprises a first optical device 150 and birefringent element 152 for focusing the first laser light to a first focus region 155 and for focusing the second laser light to a second focus region. The controller 140 receives electrical signals provided by the first detector 120 which are caused by the first self-mixing interference signal, and electrical signals provided by the second detector 121 which are caused by the second self-mixing interference signal in the second laser cavity of the second laser 121. The controller 140 further receives information from the electrical driver 130. Independent control of the first laser 110 and the second laser 111 enables parallel use of the first and second mode of the fifth laser sensor module 100. Parallel detection by means of the first laser 110 and the second laser 111 and corresponding detectors may increase the detection volume. The fifth laser sensor module 100 can obviously be combined with a movable mirror as discussed above.

Figure 6:
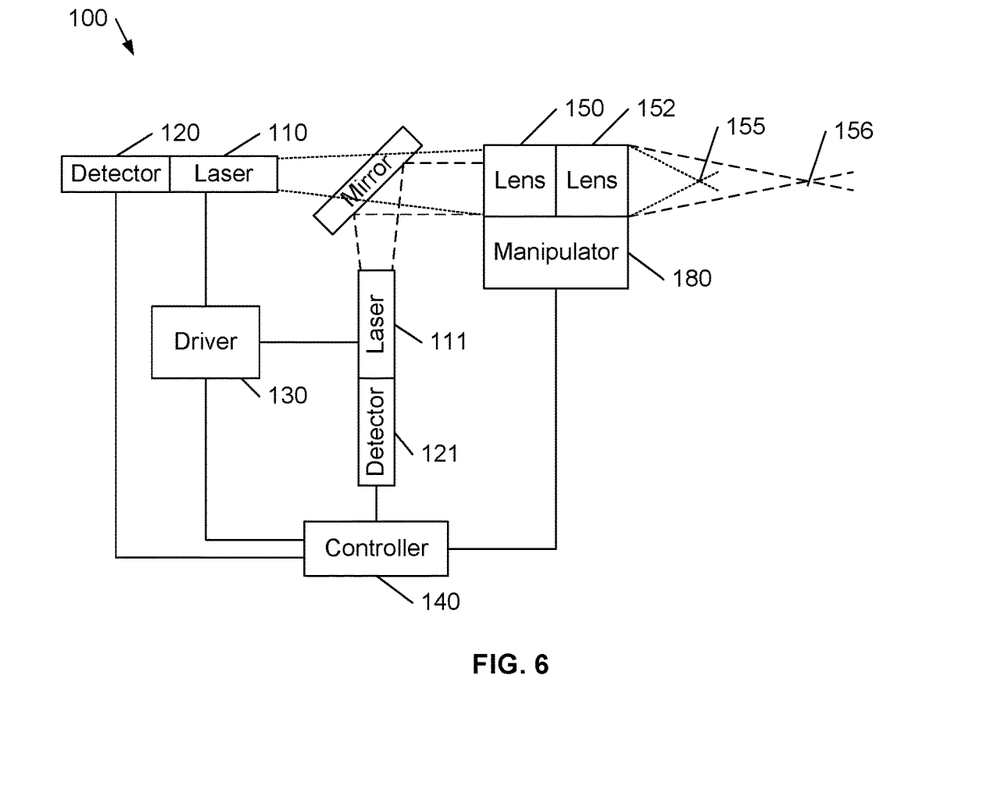
FIG. 6 shows a principal sketch of a sixth laser sensor module

FIG. 6 shows a principal sketch of a sixth laser sensor module 100. The sixth laser sensor module 100 is very similar to the fifth laser sensor module 100. The essential difference is that the first and the second laser 110, 111 are not arranged in parallel but the first laser has an optical axis which is orthogonal to an optical axis of the second laser 111. A second optical device 185 is provided in order to project the first and the second laser light to the first optical device 150 which is in this case a single focusing lens. The second optical device 185 is a polarizing beam splitter such that the first laser light is characterized by a different (orthogonal) polarization as the second laser light. The first laser light is focused to the first focus region 155. The second laser light is focused to the second focus region 156. The arrangement of the first and the second laser 110, 111 may have the advantage that a first optical distance between the first laser 110 and a first optical device 150 and the second optical distance between the second laser 111 and the first optical device 150 can be different. The distance between the first focus region 155 and the second focus region 156 may therefore be adapted by means of first and second optical distance. The sixth laser sensor module 100 can be combined with a movable mirror as discussed above.

Figure 7:
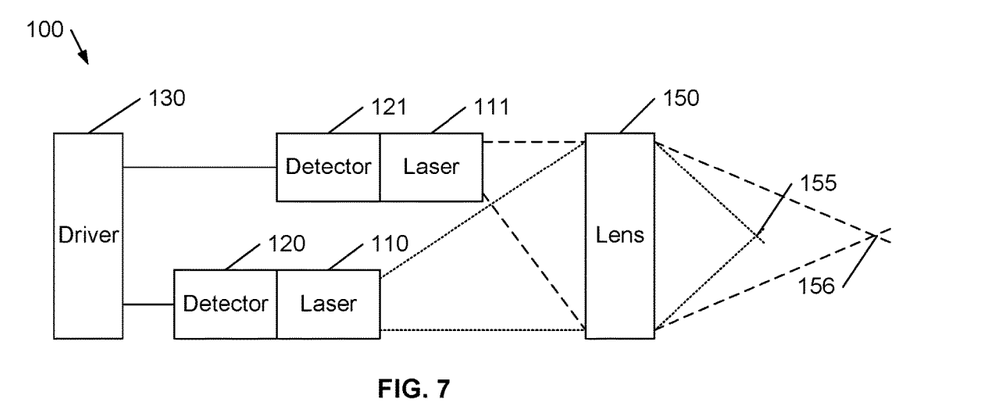
FIG. 7 shows a principal sketch of a seventh laser sensor module

FIG. 7 shows a principal sketch of a seventh laser sensor module 100. The seventh laser sensor module 100 comprises a first laser 110 with an integrated first detector 120 and a second laser 111 with an integrated second detector 121. The seventh laser sensor module 100 comprises an electrical driver 130 which is adapted to provide a drive current to the first laser 110 and to the second laser 111. The seventh laser sensor module 100 further comprises a first optical device 150 comprising in this case a lens arrangement for focusing first laser light emitted by the first laser 110 and second laser light emitted by the second laser 111. The first and the second laser 110, 111 emit non-polarized first and second laser light at a wavelength of 980 nm. A first optical distance between the first laser 110 and the first optical device 150 is different than a second optical distance between the second laser 111 and the first optical device 150. The first laser light is thus focused to the first focus region 155 and the second laser light is focused to the second focus region 156 being different than the first focus 155 region. The different optical distances enable detection of the at least two physical parameters in the first and the second mode of the seventh laser sensor module 100. The seventh laser sensor module 100 can be combined with a movable mirror as discussed above.

Figure 8:
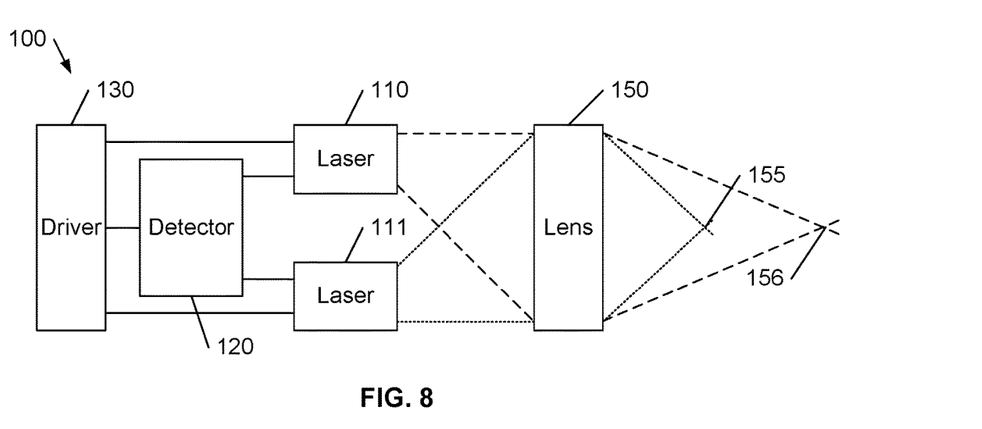
FIG. 8 shows a principal sketch of an eighth laser sensor module

FIG. 8 shows a principal sketch of an eighth laser sensor module 100. The eighth laser sensor module 100 comprises a first laser 110 and a second laser 111. The first laser 110 emits first laser light with a wavelength of 880 nm. The second laser 111 emits second laser light with a wavelength of 1050 nm. The eighth laser sensor module 100 comprises a first optical device 150. The eighth laser sensor module 100 comprises a common first detector 120. The first detector receives electrical signals from the first and the second laser 110, 111 in reaction to a first or second self-mixing interference signal. The first optical device 150 comprises a wavelength selective non-periodic structure. The first laser light is focused to a first focus region 155. The second laser light is focused to a second focus region different than the first focus region 155. The eighth laser sensor module 100 further comprises an electrical driver 130 which is adapted to provide a drive current to the first laser 110 and to the second laser 111. The drive current is provided in an alternating order to the first and the second laser 110, 111. The common first detector 120 therefore receives only one measurement signal from either the first or the second laser 110, 111 in one moment in time. The eighth laser sensor module 100 can be combined with a movable mirror as discussed above.

Figure 9:
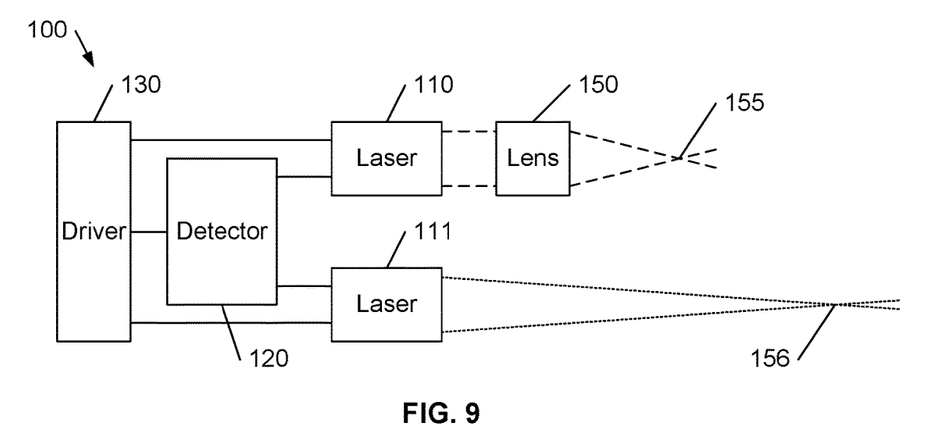
FIG. 9 shows a principal sketch of a ninth laser sensor module

FIG. 9 shows a principal sketch of a ninth laser sensor module 100. The ninth laser sensor module 100 comprises a first laser 110 and a second laser 111. The first laser 110 emits first laser light with a wavelength of 880 nm. The second laser 111 emits second laser light with a wavelength of 880 nm. The ninth laser sensor module 100 comprises a first optical device 150. The ninth laser sensor module 100 comprises a common first detector 120. The first detector receives electrical signals from the first and the second laser 110, 111 in reaction to a first or second self-mixing interference signal. The first optical device 150 comprises a lens which is positioned to focus only the first laser light emitted by the first laser 110 to the first focus region 155. The second laser 111 is arranged such that second laser light is focused to a second focus region different than the first focus region 155. The ninth laser sensor module 100 further comprises an electrical driver 130 which is adapted to provide a drive current to the first laser 110 and to the second laser 111. The drive current is provided in an alternating order to the first and the second laser 110, 111. The common first detector 120 therefore receives only one measurement signal from either the first or the second laser 110, 111 in one moment in time. The ninth laser sensor module 100 can be combined with a movable mirror as discussed above.

Figure 10:
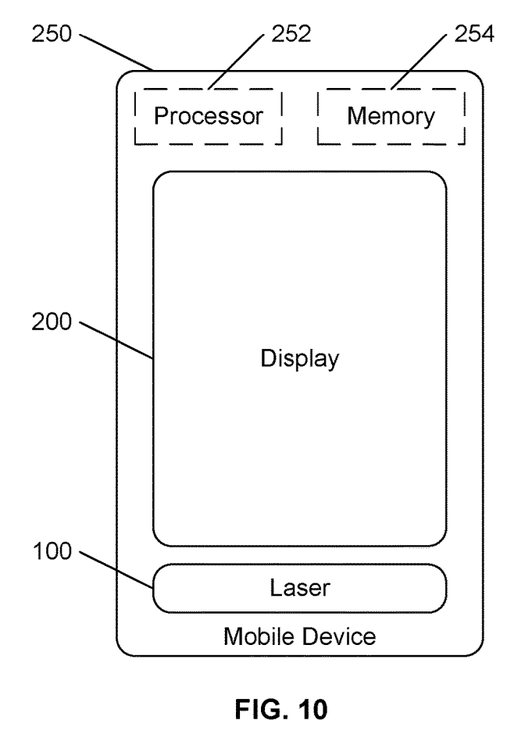
FIG. 10 shows a mobile communication device comprising a laser sensor module

FIG. 10 shows a mobile communication device 250 comprising a laser sensor module 100. The mobile communication device 250 comprises a human interface device 200 which comprises the laser sensor module 100, the mobile communication device 250 further comprises a main processing device 252 and a main memory device 253. The main processing device 252 is connected with the main memory device 253 and with laser sensor module 100. The main processing device 252 comprises at least a part of the functionalities of a controller 140 which are described above. The main processing device 252 stores data related to the first physical parameter and/or the second physical parameter in the main memory device 253. In an alternative embodiment it may also be possible that the main processing device 252 and the main memory device 253 are only used to prepare or adapt data provided by means of the laser sensor module 100 such that the data can be presented to a user of the mobile communication device 250 by means of human interface device 200. The laser sensor module 100 is powered by means of a power supply of the mobile communication device 250. The first physical parameter is related to particle detection (air pollution—PM 2.5) and the second physical parameter is related to gesture recognition as part of the human interface device 200.

Figure 11:
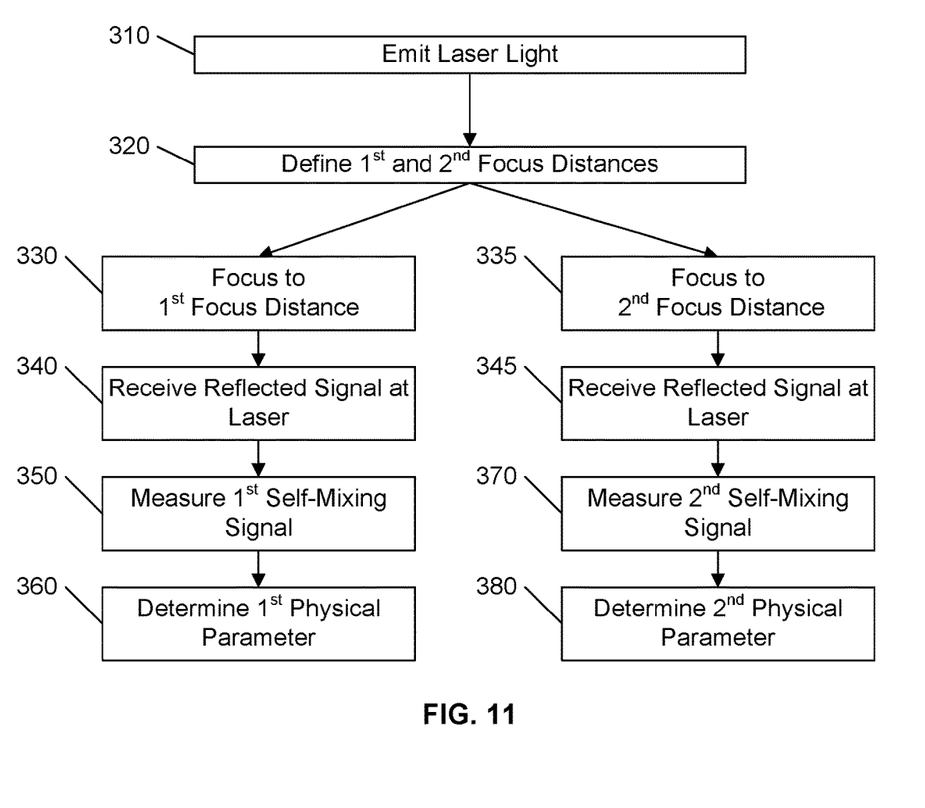
FIG. 11 shows a principal sketch of a method of detecting at least two physical parameters In the Figures, like numbers refer to like objects throughout. Objects in the Figures are not necessarily drawn to scale.

FIG. 11 shows an example method of detecting at least two physical parameters. In step 310, laser light is emitted. A distance between the laser sensor module 100 and the first and second focus regions 155, 156 are determined in step 320 such that there are at least a first mode and a second mode, wherein in the first mode the first focus region is at a first distance and in the second mode the second focus region is at a second distance different than the first distance. The laser light is focused to a first focus region in step 330. In step 340 first reflected laser light is received in the laser cavity of the laser. A first self-mixing interference signal of an optical wave within the first laser cavity of the first laser is determined in step 350, wherein the first self-mixing interference signal is caused by the first reflected first laser light reentering the first laser cavity, the first reflected laser light being received in the first laser cavity in the first mode. The first self-mixing interference signal is used in step 360 to determine the first physical parameter. The laser light is focused to the second focus region in step 335. In step 345, a second reflected laser light is received in the laser cavity of the laser. A second self-mixing interference signal is determined in step 370 in the second mode, wherein the second self-mixing interference signal is caused by second reflected laser light. The second self-mixing interference signal is used in step 380 to determine a second physical parameter different than the first physical parameter.

One of skill in the art will recognize that the particular order of steps in the method illustrated in FIG. 11 is dependent upon the particular configurations of the laser sensor module, as illustrated in FIGS. 1-9. For example, in FIGS. 1-6, the steps 330-360 are performed to obtain the first physical parameter, then the steps 335-380 are performed to determine the second physical parameter. On the other hand, in embodiments that include multiple lasers and a fixed lens, such as in FIGS. 6-7, steps 330-360 and 335-380 may be performed in parallel. In like manner, the embodiments of FIGS. 8 and 9 may perform sequential or parallel measurements, depending upon the features of the common detector 120.

It is an idea of the present invention to provide a laser sensor module which is adapted to detect or determine at least two different physical parameters by means of self-mixing interference by focusing a laser beam to different positions. Such a laser sensor module can be used as an integrated sensor module, for example, in mobile devices. The laser sensor module can be used as an input device and in addition as a sensor for detecting physical parameters in an environment of the mobile communication device. One physical parameter in the environment of the mobile communication device may, for example, be the concentration of particles in the air (air pollution, smog . . . ).

While the invention has been illustrated and described in detail in the drawings and the foregoing description, such illustration and description are to be considered illustrative or exemplary and not restrictive.

From reading the present disclosure, other modifications will be apparent to persons skilled in the art. Such modifications may involve other features which are already known in the art and which may be used instead of or in addition to features already described herein.

Variations to the disclosed embodiments can be understood and effected by those skilled in the art, from a study of the drawings, the disclosure and the appended claims. In the claims, the word "comprising" does not exclude other elements or steps, and the indefinite article "a" or "an" does not exclude a plurality of elements or steps. The mere fact that certain measures are recited in mutually different dependent claims does not indicate that a combination of these measures cannot be used to advantage.

Any reference signs in the claims should not be construed as limiting the scope thereof.

LIST OF REFERENCE NUMERALS 100 laser sensor module
110 first laser
111 second laser
120 detector
130 electrical driver
140 controller
150 first optical device
152 birefringent element
155 first focus region
156 second focus region
160 second optical device
170 first movable mirror
180 manipulation unit
185 second optical device
190 laser array
200 human interface device
250 mobile communication device
252 main processing device
253 main memory device
310 step of emitting laser light
320 step of focusing
330 step of controlling
340 step of receiving first reflected light
350 step of determining first self-mixing interference signal
360 step of using first self-mixing interference signal
370 step of determining second self-mixing interference signal
380 step of using second self-mixing interference signal

The invention claimed is:

1. A laser sensor module comprising:
   at least one first laser;
   at least one first detector;
   at least one electrical driver; and
   at least one first optical device;
   wherein the first laser is arranged to emit a first laser light based on signals provided by the at least one electrical driver,
   wherein the first optical device is arranged to focus the first laser light on a focus region,
   wherein the laser sensor module is arranged to control a distance between the laser sensor module and the focus region such that there are at least a first mode and a second mode of the laser sensor module,
   wherein in the first mode the focus region is at a first distance and in the second mode the focus region is at a second distance,
   wherein the second distance is different than the first distance,
   wherein the at least one first detector is arranged to detect a first self-mixing interference signal of an optical wave within a first laser cavity of the first laser,
   wherein the first self-mixing interference signal is caused by a first reflected laser light reentering the first laser cavity,
   wherein the first reflected laser light is received in the first mode,
   wherein the first self-mixing interference signal is used to determine a first physical parameter,
   wherein the first physical parameter is related to a movement of an object,
   wherein the laser sensor module is arranged to detect a second self-mixing interference signal contemporaneously with detecting the first self-mixing signal,
   wherein the second self-mixing interference signal is caused by a second reflected laser light,
   wherein the second self-mixing interference signal is determined in the second mode,
   wherein the second self-mixing interference signal is used to determine a second physical parameter being related to a detection of a particle density or a particle size,
   wherein the second physical parameter is different than the first physical parameter.

2. The laser sensor module according to claim 1,
   wherein the laser sensor module is arranged to provide a quasi-collimated beam of the first laser light in the first mode,
   wherein the laser sensor module is arranged to focus laser light in the second mode to a spot.

3. The laser sensor module according to claim 1,
   wherein the laser sensor module comprises a manipulation apparatus,
   wherein the manipulation apparatus is arranged to change a characteristic of the first laser light such that the first mode and the second mode are enabled.

4. The laser sensor module according to claim 3, further comprising a controller circuit, wherein the controller circuit is arranged to provide control signals for controlling the manipulation apparatus such that the first laser light is focused in a first focus region in the first mode and the first laser light is focused in a second focus region in the second mode.

5. The laser sensor module according to claim 4,
   wherein the first optical device comprises the manipulation apparatus,
   wherein the manipulation apparatus is arranged to provide at least a first focal length of the first optical device and a second focal length of the first optical device,
   wherein the second focal length is different than the first focal length,
   wherein the controller circuit is arranged to provide control signals for controlling the manipulation apparatus such that the first optical device provides the first focal length in the first mode and the second focal length in the second mode.

6. The laser sensor module according to claim 3,
   wherein the laser sensor module comprises at least a second laser,
   wherein the second laser is arranged to emit second laser light in reaction to signals provided by the at least one electrical driver,
   wherein a first optical distance between the first laser and the first optical device is different than a second optical distance between the second laser and the first optical device,
   wherein the manipulation apparatus is arranged to image the first laser light using the first optical device to a first focus region in the first mode,
   wherein the manipulation apparatus is arranged to focus the second laser light using the first optical device to a second focus region in the second mode,
   wherein the second focus region is different than the first focus region.

7. The laser sensor module according to claim 3, wherein the manipulation apparatus is arranged to change an optical distance between the first laser and the first optical device.

8. The laser sensor module according to claim 1,
   wherein the first optical device comprises at least one birefringent element,
   wherein the at least one birefringent element enables the first mode and the second mode.

9. The laser sensor module according to claim 8,
   wherein the laser sensor module comprises a controller circuit,
   wherein the first laser is arranged to emit the first laser light with a first polarization and a second polarization,
   wherein the second polarization is different than the first polarization,
   wherein the controller circuit is arranged to provide control signals for controlling the first laser such that the first laser emits the first laser light with the first polarization in the first mode and the first laser light with the second polarization in the second mode,
   wherein the at least one birefringent element is arranged to focus the first laser light with the first polarization on a first focus region,
   wherein the at least one birefringent element is arranged to focus the first laser light with the second polarization on a second focus region,
   wherein the second focus region is different than the first focus region.

10. The laser sensor module according to claim 1, wherein the first optical device is arranged to focus a first part of the first laser light on a first focus region and a second part of the first laser light on a second focus region.

11. The laser sensor module according to claim 1,
    wherein the laser sensor module further comprises at least a second laser,
    wherein the second laser is arranged to emit second laser light via the first optical device based on signals provided by the at least one electrical driver, wherein the first laser light comprises a first wavelength and the second laser light comprises a second wavelength, wherein the second wavelength is different than the first wavelength, wherein the first optical device is arranged to focus the first laser light on a first focus region in the first mode, wherein the first optical device is arranged to focus the second laser light on a second focus region in the second mode, wherein the second focus region is different than the first focus region.

12. A human interface apparatus comprising at least one laser sensor module according to claim 1, wherein the first mode of the laser sensor module is arranged to enable at least a part of an input feature provided by the human interface device.

13. A mobile communication device comprising at least one human interface device according to claim 12.

14. The laser sensor module according to claim 1, wherein the movement of the object is arranged for gesture control.

15. A method of contemporaneously detecting at least two physical parameters, the method comprising the steps of:
emitting a first laser light from a first laser;
focusing the first laser light on a focus region;
controlling a distance between the laser sensor module and the focus region such that there are at least a first mode and a second mode,
wherein in the first mode the focus region is at a first distance and in the second mode the focus region is at a second distance,
wherein the second distance is different than the first distance;
receiving a first reflected laser light in a first laser cavity of the first laser;
determining a first self-mixing interference signal of an optical wave within the first laser cavity of the first laser,
wherein the first self-mixing interference signal is caused by the first reflected first laser light reentering the first laser cavity,
wherein the first reflected laser light is received in the first laser cavity in the first mode;
determining the first physical parameter using the first self-mixing interference signal,
wherein the first physical parameter is related to a movement of an object;
determining a second self-mixing interference signal in the second mode,
wherein the second self-mixing interference signal is caused by second reflected laser light; and
using the second self-mixing interference signal to determine a second physical parameter,
wherein the second physical parameter is different than the first physical parameter,
wherein the second physical parameter is related to a detection of a particle density or a particle size.

16. A computer program product comprising code wherein the code is arranged such that the method according to claim 15 can be executed using at least one processing device comprised by a laser sensor module.

17. The method according to claim 15, wherein the movement of the object is arranged for gesture control.

18. The method according to claim 15,
wherein the first laser light is arranged in a quasi-collimated beam in the first mode,
wherein the focusing of the first laser light is focused to a spot in the second mode.

19. The method according to claim 15 further comprising changing a characteristic of the first laser light such that the first mode and the second mode are enabled.

20. The method according to claim 15 further comprising:
focusing the first laser light in a first focus region in the first mode; and
focusing the first laser light in a second focus region in the second mode.

* * * * *